United States Patent
Parker et al.

(10) Patent No.: US 7,601,795 B2
(45) Date of Patent: *Oct. 13, 2009

(54) PROCESS FOR PRODUCTION OF A CARBOXYLIC ACID/DIOL MIXTURE SUITABLE FOR USE IN POLYESTER PRODUCTION

(75) Inventors: Kenny Randolph Parker, Afton, TN (US); Robert Lin, Kingsport, TN (US); Philip Edward Gibson, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 475 days.

This patent is subject to a terminal disclaimer.

(21) Appl. No.: 11/076,839

(22) Filed: Mar. 10, 2005

(65) Prior Publication Data
US 2005/0159617 A1 Jul. 21, 2005

Related U.S. Application Data

(63) Continuation-in-part of application No. 10/758,678, filed on Jan. 15, 2003, now Pat. No. 7,214,760.

(51) Int. Cl.
*C08G 64/10* (2006.01)
*C07C 51/255* (2006.01)
*C07C 51/16* (2006.01)

(52) U.S. Cl. .................. 528/272; 562/412; 422/135; 422/131; 526/62; 526/71

(58) Field of Classification Search .......... 562/412; 528/272
See application file for complete search history.

(56) References Cited

U.S. PATENT DOCUMENTS

| | | | |
|---|---|---|---|
| 3,057,909 A * | 10/1962 | Sebelist et al. | 560/94 |
| 3,064,044 A | 11/1962 | Baldwin | |
| 3,584,039 A | 6/1971 | Meyer | |
| 3,683,018 A | 8/1972 | Longland, Jr. | |
| 3,839,436 A | 10/1974 | Longland, Jr. | |
| 3,850,983 A | 11/1974 | Park | |

(Continued)

FOREIGN PATENT DOCUMENTS

CA 1067095 11/1979

(Continued)

OTHER PUBLICATIONS

USPTO Office Action dated Mar. 3, 2006 for U.S. Appl. No. 10/383,126.
USPTO office action dated Nov. 1, 2006 for copending U.S. Appl. No. 10/271,058.
USPTO Office Action dated May 7, 2007 for copending U.S. Appl. No. 11/076,840.

(Continued)

*Primary Examiner*—Daniel M Sullivan
*Assistant Examiner*—Kellette Gale
(74) *Attorney, Agent, or Firm*—Steven A. Owen; Bernard J. Graves, Jr.

(57) ABSTRACT

The present invention relates to a process by which a carboxylic acid/diol mixture is obtained from a slurry or cake carboxylic acid product without isolation of a substantially dry carboxylic acid solid. More specifically, the present invention relates to a process by which a terephthalic acid/ethylene glycol mixture suitable as a starting material for polyester or co-polyester production is obtained from a slurry or cake terephthalic acid product without isolation of a substantially dry terephthalic acid solid.

30 Claims, 2 Drawing Sheets

U.S. PATENT DOCUMENTS

| | | | |
|---|---|---|---|
| 3,931,305 A | 1/1976 | Fisher | |
| 4,051,178 A | 9/1977 | Kimura et al. | |
| 4,201,871 A | 5/1980 | Tanouchi et al. | |
| 4,212,995 A | 7/1980 | Shiraki | |
| 4,268,690 A | 5/1981 | Komatsu et al. | |
| 4,330,676 A | 5/1982 | Moxham | |
| 4,334,086 A | 6/1982 | Hanotier et al. | |
| 4,357,475 A | 11/1982 | Hanotier et al. | |
| 4,380,662 A | 4/1983 | Hanotier et al. | |
| 4,500,732 A | 2/1985 | Petty-Weeks et al. | |
| 4,588,414 A | 5/1986 | Takegami et al. | |
| 4,707,274 A | 11/1987 | Donhauser et al. | |
| 4,782,181 A * | 11/1988 | James | 562/487 |
| 4,812,233 A | 3/1989 | Coenen et al. | |
| 4,861,919 A | 8/1989 | Robbins et al. | |
| 4,892,972 A | 1/1990 | Schroeder et al. | |
| 4,939,297 A | 7/1990 | Browder et al. | |
| 5,008,450 A | 4/1991 | Yamamoto et al. | |
| 5,080,721 A | 1/1992 | Flanigan et al. | |
| 5,095,146 A | 3/1992 | Zeitlin et al. | |
| 5,107,874 A | 4/1992 | Flanigan et al. | |
| 5,116,423 A | 5/1992 | Kokkonen et al. | |
| 5,143,554 A | 9/1992 | Koyama et al. | |
| 5,175,355 A | 12/1992 | Streich et al. | |
| 5,200,557 A | 4/1993 | Gee et al. | |
| 5,454,959 A | 10/1995 | Stevens | |
| 5,476,919 A | 12/1995 | Schaeffer | |
| 5,527,957 A | 6/1996 | Hindmarsh et al. | |
| 5,563,293 A | 10/1996 | Hindmarsh et al. | |
| 5,567,842 A | 10/1996 | Izumisawa et al. | |
| 5,583,254 A | 12/1996 | Turner et al. | |
| 5,616,792 A | 4/1997 | Bartos et al. | |
| 5,635,074 A | 6/1997 | Stenstrom et al. | |
| 5,643,468 A | 7/1997 | Ure | |
| 5,653,673 A | 8/1997 | Desai et al. | |
| 5,676,847 A | 10/1997 | Yamamoto et al. | |
| 5,679,846 A | 10/1997 | Hindmarsh et al. | |
| 5,684,187 A | 11/1997 | Ohkoshi et al. | |
| 5,698,734 A | 12/1997 | Turner et al. | |
| 5,712,412 A | 1/1998 | Inary et al. | |
| 5,777,161 A | 7/1998 | Inary | |
| 5,840,965 A | 11/1998 | Turner et al. | |
| 5,840,968 A | 11/1998 | Lee et al. | |
| 5,925,786 A | 7/1999 | Isayama et al. | |
| 5,955,394 A | 9/1999 | Kelly | |
| 5,971,907 A | 10/1999 | Johannemann et al. | |
| 5,973,196 A | 10/1999 | Takano et al. | |
| 6,013,835 A | 1/2000 | Lee et al. | |
| 6,153,790 A | 11/2000 | June et al. | |
| 6,162,837 A | 12/2000 | Gerking et al. | |
| 6,228,215 B1 | 5/2001 | Hoffman, Jr. | |
| 6,297,348 B1 | 10/2001 | Rodden et al. | |
| 6,307,099 B1 | 10/2001 | Turner et al. | |
| 6,495,044 B1 | 12/2002 | Verdoes | |
| 6,517,733 B1 | 2/2003 | Carlson | |
| 6,797,073 B1 | 9/2004 | Teruggi et al. | |
| 7,193,109 B2 * | 3/2007 | Lin et al. | 562/485 |
| 2003/0004372 A1 | 1/2003 | Piras et al. | |
| 2004/0073059 A1 | 4/2004 | Lin | |
| 2004/0176635 A1 | 9/2004 | Lin et al. | |
| 2004/0245176 A1 | 12/2004 | Parker et al. | |
| 2005/0087215 A1 | 4/2005 | Miyahara et al. | |
| 2005/0159578 A1 | 7/2005 | Parker et al. | |

FOREIGN PATENT DOCUMENTS

| | | | |
|---|---|---|---|
| CN | 1299806 | | 6/2001 |
| DE | 31 28 474 | | 6/1982 |
| DE | 33 28 543 | | 3/1985 |
| EP | 0 370 083 | | 6/1994 |
| GB | 994 769 | | 6/1965 |
| GB | 1059840 | | 2/1967 |
| GB | 1334452 | | 10/1973 |
| GB | 1498031 | | 1/1978 |
| GB | 1589310 | | 5/1981 |
| JP | 48-15848 | | 2/1973 |
| JP | 48026740 | | 4/1973 |
| JP | 48-67239 | | 9/1973 |
| JP | 52-113940 | | 11/1977 |
| JP | 53-53634 | | 5/1978 |
| JP | 53-90233 | | 8/1978 |
| JP | 53-90234 | | 8/1978 |
| JP | 55-33421 | | 3/1980 |
| JP | 7-149690 | | 6/1995 |
| JP | 7-291896 | | 11/1995 |
| JP | 9-255619 | | 9/1997 |
| JP | 9-286758 | | 11/1997 |
| JP | 9-286759 | | 11/1997 |
| JP | 10-36313 | | 2/1998 |
| JP | 2003-62405 | | 3/2003 |
| JP | 2003-128624 | | 5/2003 |
| SU | 1042809 | | 1/1971 |
| WO | WO 93/24440 | | 12/1993 |
| WO | WO 97/17391 | * | 5/1997 |
| WO | WO 97/17391 A | | 5/1997 |
| WO | WO 98/38150 | | 9/1998 |
| WO | WO 99/08990 | | 2/1999 |
| WO | WO 03/020680 | | 3/2003 |

OTHER PUBLICATIONS

USPTO Office Action dated Mar. 19, 2007, for copending U.S. Appl. No. 10/271,058.

M. Matias, R. Bacai Oglu, R.F. Paie & H.H. Glatt, "Study of Di- and Polyesterification, I. Esterification of Ethylene and Diethylene Glycols with Acetic Acid", (1978), Chemical Bulletin of the Technical University of Timisoara, 23(37), pp. 73-76.

Arun Pal Aneja and Viney Pal Aneja, "The Effect of Water and Air Contamination on Poly (Ethylene Terephthalate) Formation", *Polymer Engineering Reviews*, 1982, pp. 123-133, vol. 2, No. 2.

Allen, Norman S., Edge, Michele, Daniels, James, Royall, David, "*Spectroscopic Analysis of Organic Contaminants in Terphthalic Acid: Colour Implications in Poly(ethylene terephthalate) Manufacture* ", Polymer Degradation and Stability, 1998, pp. 373-383, 62, Great Britain.

USPTO Office Action for U.S. Appl. No. 10/271,058 dated Apr. 6, 2004.

USPTO Office Action for U.S. Appl. No. 10/383,126 dated Jun. 28, 2004.

USPTO Notice of Allowability for U.S. Appl. No. 10/758,678 dated Jul. 6, 2004.

USPTO Office Action for U.S. Appl. No. 10/271,058 dated Jul. 15, 2004.

USPTO Office Action for U.S. Appl. No. 10/758,678 dated Dec. 8, 2004.

USPTO Office Action for U.S. Appl. No. 10/383,126 dated Dec. 22, 2004.

USPTO Office Action for U.S. Appl. No. 10/271,058 dated Dec. 22, 2004.

USPTO Office Action for U.S. Appl. No. 10/758,678 dated Jun. 29, 2005.

USPTO Office Action dated Oct. 3, 2004 for Application No. 11/077/481.

USPTO Office Action dated May 30, 2006 for U.S.Appl. No. 11/077,481.

USPTO office action dated Aug. 4, 2006 for copending U.S. Appl. No. 10/758,678.

USPTO Office Action dated Sep. 14, 2005 for copending U.S. Appl. No. 11/077,481.

USPTO Notice of Allowance dated Dec. 28, 2007 for copending U.S. Appl. No. 11/076,840.

* cited by examiner

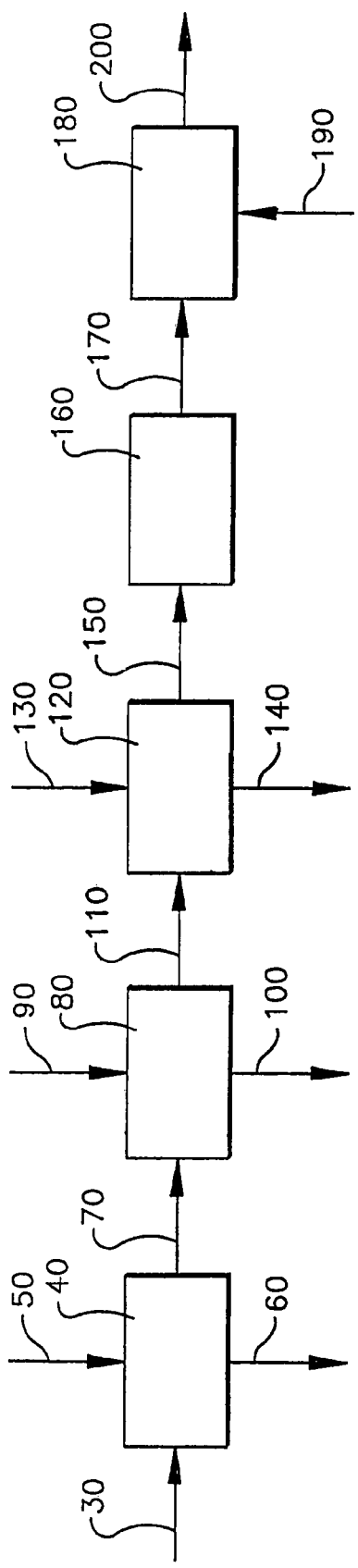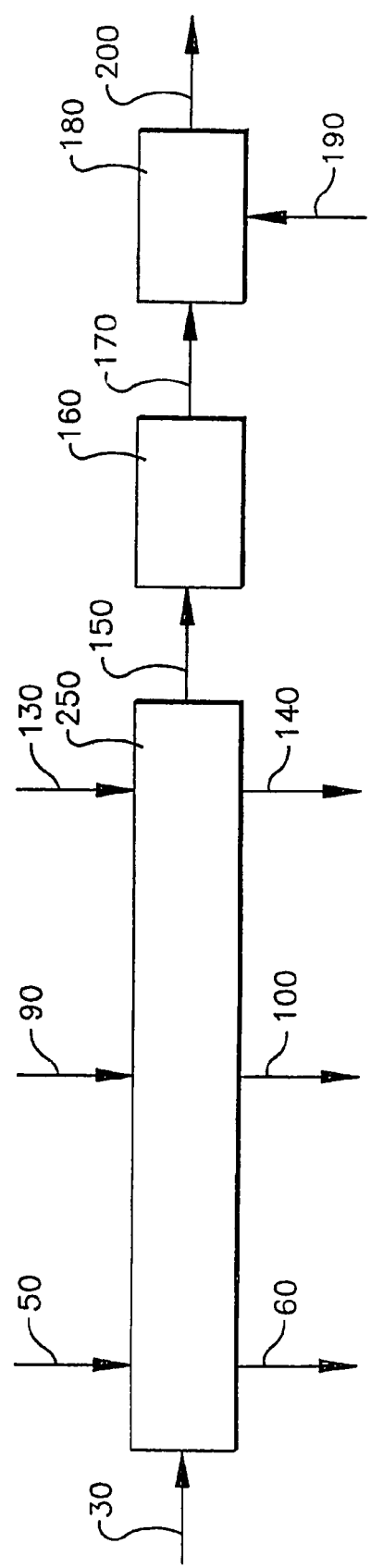

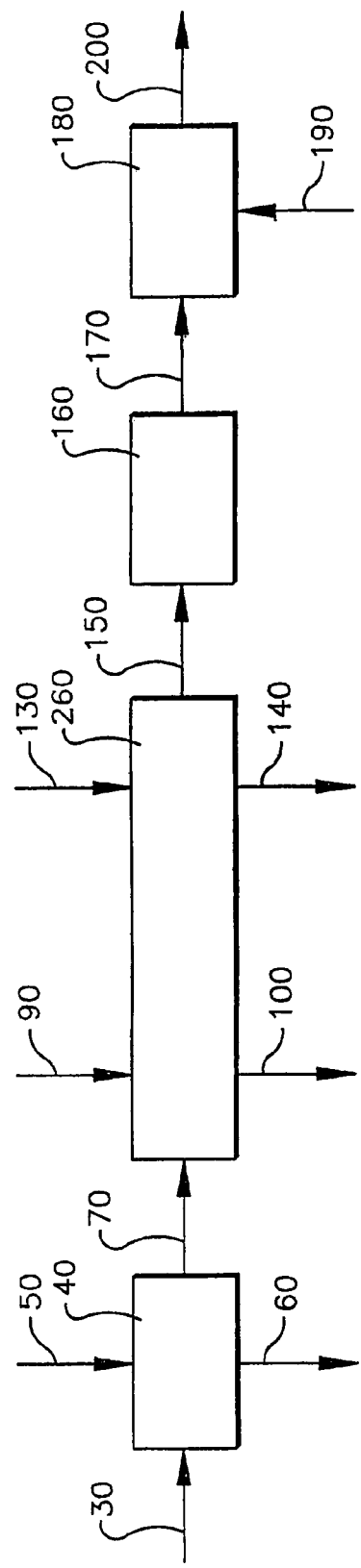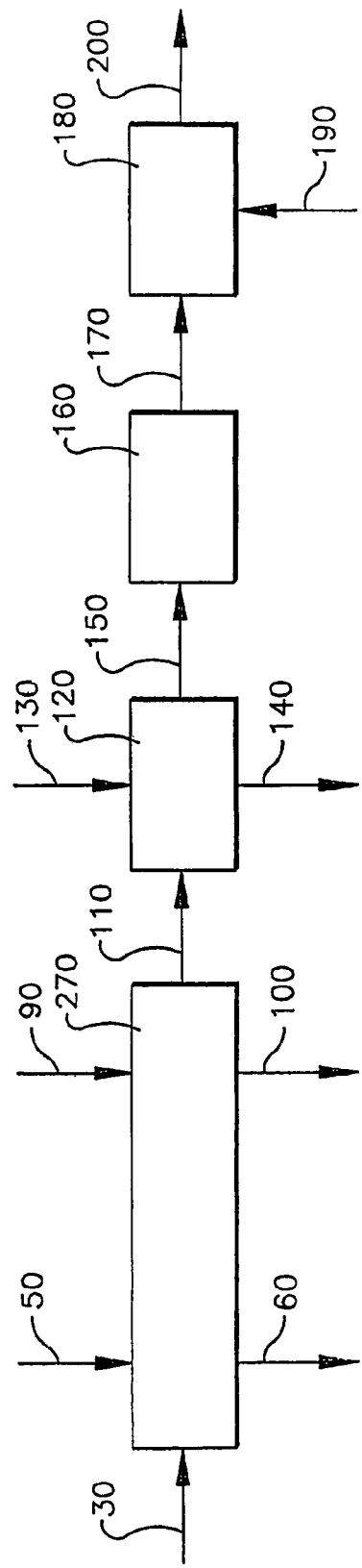

PROCESS FOR PRODUCTION OF A CARBOXYLIC ACID/DIOL MIXTURE SUITABLE FOR USE IN POLYESTER PRODUCTION

CROSS REFERENCE TO RELATED APPLICATION

This application is a continuation-in-part of U.S. application Ser. No. 10/758,678, filed Jan. 15, 2003 now U.S. Pat. No. 7,214,760, hereby incorporated by reference in its entirety to the extent that they do not contradict statements herein.

FIELD OF INVENTION

The present invention relates to a process by which a carboxylic acid/diol mixture is obtained from a slurry or cake carboxylic acid product without isolation of a substantially dry carboxylic acid solid. More specifically, the present invention relates to a process by which a terephthalic acid/diol mixture suitable as a starting material for polyester or co-polyester production is obtained from a slurry or cake terephthalic acid product without isolation of a substantially dry terephthalic acid solid.

BACKGROUND OF THE INVENTION

Pursuant to the goal of making polyethylene terephthalate (PET) and other polyesters or co-polyesters, a great deal of patent literature is dedicated to describing the processes for preparing a carboxylic acid/diol mixture suitable as starting material. In general, these inventions describe specific mixing schemes with a purified terephthalic acid solid and liquid ethylene glycol. Additionally, there is substantial body of literature devoted to describing the production of a purified terephthalic acid in powder form that is suitable for use in producing PET and other polyesters or co-polyesters.

The objective of this invention is to describe a process by which the carboxylic acid/diol mixture suitable as a starting material for polyester or co-polyester production is obtained from a slurry or cake carboxylic acid product without isolation of a substantially dry carboxylic acid solid. More specifically, the objective of this invention is to describe a process by which a terephthalic acid/diol mixture suitable as a starting material for polyester or co-polyester production is obtained from a slurry or cake terephthalic acid product without isolation of a substantially dry terephthalic acid solid.

Usually, purified terephthalic acid solid is produced in a multi-step process wherein a crude terephthalic acid is produced. Liquid phase oxidation of p-xylene produces crude terephthalic acid. The crude terephthalic acid does not have sufficient quality for direct use as starting material in commercial PET. Instead, the crude terephthalic acid is usually refined to purified terephthalic acid solid.

Usually, in terephthalic acid purification processes, the crude terephthalic acid is dissolved in water and hydrogenated for the purpose of converting 4-carboxybenzaldehyde to p-toluic acid, which is a more water-soluble derivative, and for the purpose of converting characteristically yellow compounds to colorless derivatives. Significant 4-carboxybenzaldehyde or p-toluic acid in the final purified terephthalic acid product is particularly detrimental to polymerization processes as each can act as a chain terminator during the condensation reaction between terephthalic acid and ethylene glycol in the production of PET. Typical purified terephthalic acid contains on a weight basis less than 25 parts per million (ppm) 4-carboxybenzaldehyde and less than 150 ppm p-toluic acid.

A number of other processes have been developed where a terephthalic acid suitable as starting material for commercial PET production is produced without the use of hydrogenation. Typically, terephthalic acid production processes usually involve catalyzed oxidation of p-xylene in an acetic acid solvent followed by filtration and drying of the terephthalic acid.

To produce a terephthalic acid/diol mixture acceptable for PET production from a slurry or cake terephthalic acid product poses a substantially different problem than from a dry terephthalic acid powder.

Typically, terephthalic acid (TPA) produced via catalyzed oxidation of p-xylene in an acetic acid solvent produces a slurry or cake terephthalic acid product that contains residual catalyst (e.g cobalt, manganese, and bromine compounds). In a common method of producing a substantially dry TPA solid from a slurry or cake terephthalic acid product, the slurry or cake terephthalic acid product is filtered to separate a substantial amount of the acetic acid liquid from the TPA solids. Residual catalyst is usually separated from the slurry or cake terephthalic acid product by washing (rinsing) the wet cake with catalyst-free acetic acid, water or other solvent. The TPA solid is isolated by drying.

In the present invention, a novel process has been discovered resulting in fewer steps than the currently employed processes. The primary utility of the invention is reduction of capital and operating costs associated with the isolation and drying of a terephthalic acid powder. In the conventional approach toward producing terephthalic acid via catalyzed oxidation of p-xylene in an acetic acid solvent, a slurry or cake terephthalic acid product is filtered, washed, then dried to produce a terephthalic acid powder suitable as starting material for PET production.

In one embodiment of the present invention, the slurry or cake terephthalic acid product is filtered to produce a terephthalic acid cake with solvent and a solvent mother liquor stream. The terephthalic acid cake with solvent is then washed (rinsed) with water to recover residual metal catalyst material and to produce a water-wet terephthalic acid cake and a solvent/water by-product liquor. The water-wet terephthalic acid cake is then combined with a diol to produce a terephthalic acid/diol mixture suitable as starting material in a commercial PET process. By eliminating conventional processes for isolating and drying a terephthalic acid solid, the equipment and energy necessary to produce a terephthalic acid powder is also eliminated.

Another surprising and seemingly contradictory aspect of the invention is the benefit of addition of water to the acetic acid and ethylene glycol solvents. In general, in conventional processes for producing terephthalic acid, it is necessary to remove water produced in the oxidation process. Typically, use of acetic acid as an oxidation solvent necessitates an additional process step where acetic acid and water are separated. It is seemingly contradictory to produce an acetic acid and water mixture when it can be avoided by drying the terephthalic acid from the acetic acid solvent.

Additionally, in processes for producing PET via esterification of TPA with ethylene glycol, water is generated as a reaction by-product. In general, it is necessary to remove the water produced in the esterification process via an additional process step where ethylene glycol and water are separated. It is seemingly contradictory to produce an ethylene glycol and water mixture when it can be avoided by not introducing water with the TPA. However, a benefit of this invention is based on the premise that ethylene glycol/water and acetic acid/water separation systems normally exist for conventional TPA and PET production processes. In this invention, the value associated with eliminating the TPA drying can be of great benefit when compared to traditional TPA production processes.

SUMMARY OF THE INVENTION

The present invention relates to a process by which a carboxylic acid/diol mixture is obtained from a slurry or cake carboxylic acid product without isolation of a substantially dry carboxylic acid solid. More specifically, the present invention relates to a process for the production of a terephthalic acid/ethylene glycol mixture suitable as feedstock for the production of commercial PET. The resulting process can save energy and has fewer steps than currently employed processes. Specifically, the present invention incorporates a direct displacement of water with ethylene glycol. Incorporation of the displacement step eliminates the need to isolate a purified terephthalic acid solid and could eliminate the need for crystallization, solid-liquid separation, drying and solids handling equipment normally found in commercial purified terephthalic acid processes.

It is an object of this invention to provide a process for producing a carboxylic acid/diol mixture from a slurry or cake carboxylic acid product without isolation of a substantially dry carboxylic acid solid.

It is an object of this invention to provide a process for producing a carboxylic acid/diol mixture from a slurry or cake carboxylic acid product suitable as starting material for the production of polyesters or co-polyesters without isolation of a substantially dry carboxylic acid solid.

It is another object of this invention to provide a process for producing a terephthalic acid/diol mixture from a slurry or cake terephthalic acid product without isolation of a substantially dry terephthalic acid solid.

It is another object of this invention to provide a process for producing a terephthalic acid/ethylene glycol mixture from a terephthalic acid solvent slurry or cake without isolation of a substantially dry terephthalic acid solid.

It is another object of this invention to provide a process for producing a terephthalic acid/ethylene glycol mixture without isolation of a substantially dry terephthalic acid solid by removing water from a water-wet terephthalic acid cake through the use of a carboxylic acid/diol mixing zone.

In a first embodiment of this invention, a process for producing a carboxylic acid/diol mixture is provided, the process comprises:

(a) removing in a liquor exchange zone impurities from a carboxylic acid slurry to form a water-wet carboxylic acid cake, a mother liquor stream, a solvent mother liquor stream, and a solvent/water byproduct liquor stream;

(b) routing the water-wet carboxylic acid cake to a vapor seal zone; and (c) adding at least one diol to the water-wet carboxylic acid cake in a carboxylic acid/diol mixing zone to remove a portion of the water to form the carboxylic acid/diol mixture.

In another embodiment of this invention, a process for producing a carboxylic acid/diol mixture is provided, the process comprises:

(a) removing in a solvent liquor exchange zone impurities from a carboxylic acid slurry to form a carboxylic acid cake with solvent, a mother liquor stream, and a solvent mother liquor stream;

(b) adding water in a water wash zone to the carboxylic cake with solvent to produce a water-wet carboxylic acid cake and a solvent/water by product liquor stream;

(c) routing the water-wet carboxylic acid cake to a vapor seal zone; and (d) adding at least one diol to the water-wet carboxylic acid cake in a carboxylic acid/diol mixing zone to remove a portion of the water to form the carboxylic acid/diol mixture.

In another embodiment of this invention, a process for producing a carboxylic acid/diol mixture is provided, the process comprises:

(a) removing in a solid-liquid separation zone impurities from a carboxylic acid slurry to form a slurry or cake carboxylic acid product and a mother liquor stream;

(b) removing in a solvent-water liquor exchange zone impurities from the slurry or cake carboxylic acid product to form a water-wet carboxylic acid cake, a solvent mother liquor stream, and a solvent/water byproduct liquor stream;

(c) routing the water-wet carboxylic acid cake to a vapor seal zone; and (d) adding at least one diol to the water-wet carboxylic acid cake in a carboxylic acid/diol mixing zone to remove a portion of the water to form the carboxylic acid/diol mixture.

In another embodiment of this invention, a process for producing a carboxylic acid/diol mixture is provided, the process comprises:

(a) removing a solvent from a slurry or cake carboxylic acid product in a solvent-water liquor exchange zone; wherein a portion of the solvent in the slurry or cake carboxylic acid product is replaced with water to form a water-wet carboxylic acid cake;

(b) routing the water-wet carboxylic acid cake to a vapor seal zone; and (c) adding at least one diol to the water-wet carboxylic acid cake in a carboxylic acid/diol mixing zone to remove a portion of the water to form the carboxylic acid/diol mixture.

In another embodiment of this invention, a process for producing a terephthalic acid/diol mixture is provided, the process comprises:

(a) removing in a solvent wash zone impurities from a slurry or cake terephthalic acid product to form a terephthalic acid cake with acetic acid;

(b) removing a portion of a solvent in a water wash zone from the terephthalic acid cake with acetic acid to form a water-wet terephthalic acid cake; and (c) routing the water-wet terephthalic acid cake to a vapor seal zone; and (d) adding at least one diol to the water-wet terephthalic acid cake in a carboxylic acid/diol mixing zone to remove a portion of the water to form the terephthalic acid/diol mixture.

In another embodiment of this invention, a process for producing a terephthalic acid/diol mixture is provided, the process comprises:

(a) removing a solvent from a slurry or cake terephthalic acid product in a solvent liquor exchange zone; wherein a portion of the solvent in the slurry or cake terephthalic acid product is replaced with water to form a water-wet terephthalic acid cake;

(b) routing the water-wet terephthalic acid cake to a vapor seal zone; and (c) adding at least one diol to the water-wet terephthalic acid cake in a carboxylic acid/diol mixing zone to remove a portion of the water to form the terephthalic acid/diol mixture.

In another embodiment of this invention, a process for producing a terephthalic acid/diol mixture is provided, the process comprises:

(a) removing in a solvent wash zone impurities from a slurry or cake terephthalic acid product from a terephthalic acid cake with acetic acid; wherein the solvent wash zone comprises at least one solid-liquid separation device that is operated at a temperature between about 40° C. to about 155° C.;

(b) removing a portion of a solvent in a water wash zone from the terephthalic acid cake with acetic acid to form a water-wet terephthalic acid cake; wherein the water wash zone comprises at least one solid-liquid separation device that is operated at a temperature between about 40° C. to about 155° C.;

(c) adding at least one diol to the water-wet terephthalic acid cake in a carboxylic acid/diol mixing zone to remove a portion of the water to form the terephthalic acid/diol mixture; wherein the adding occurs at a temperature between about 40° C. to about 290° C.; wherein the diol is ethylene glycol.

In another embodiment of this invention, a process for producing a carboxylic acid/diol mixture is provided, the process comprises:

(a) removing in a solid-liquid separation zone impurities from a carboxylic acid slurry to form a slurry or cake carboxylic acid product and a mother liquor stream;

(b) adding solvent to a slurry or cake carboxylic acid product in a solvent wash zone to the slurry or cake carboxylic acid product to produce a carboxylic acid cake with solvent and a solvent mother liquor stream;

(c) adding water in a water wash zone to the carboxylic acid cake with solvent to produce a water-wet carboxylic acid cake and a solvent/water by product liquor stream;

(d) routing the water-wet carboxylic acid cake to a vapor seal zone; and (e) adding at least one diol to the water-wet carboxylic acid cake in a carboxylic acid/diol mixing zone to remove a portion of the water to form the carboxylic acid/diol mixture.

In another embodiment of this invention, a process for producing a terephthalic acid/diol mixture is provided, the process comprises:

(a) removing in a solid-liquid separation zone impurities from a crude terephthalic acid slurry to form a slurry or cake terephthalic acid product and a mother liquor stream;

(b) adding solvent in a solvent wash zone to the slurry or cake terephthalic acid product to produce a terephthalic acid cake with solvent and a solvent mother liquor stream;

(c) adding water in a water wash zone to the terephthalic acid cake with solvent to produce a water-wet terephthalic acid cake and a solvent/water by product liquor stream;

(d) routing the water-wet terephthalic acid cake to a vapor seal zone; and (e) adding at least one diol to the water-wet terephthalic acid cake in a carboxylic acid/diol mixing zone to remove a portion of the water to form the terephthalic acid/diol mixture.

These objects, and other objects, will become more apparent to others with ordinary skill in the art after reading this disclosure.

BRIEF DESCRIPTION OF THE DRAWINGS

FIG. 1 illustrates one embodiment of this invention, a process for producing a carboxylic acid/diol mixture.

FIG. 2 illustrates another embodiment of this invention, a process for producing a carboxylic acid/diol mixture by utilizing a liquor exchange zone.

FIG. 3 illustrates another embodiment of this invention, a process for producing a carboxylic acid/diol mixture by utilizing a solvent-water liquor exchange zone.

FIG. 4 illustrates another embodiment of this invention, a process for producing a carboxylic acid/diol mixture by utilizing a solvent liquor exchange zone.

DESCRIPTION OF THE INVENTION

In an embodiment of this invention shown in FIG. 1, a process for producing a carboxylic acid/diol mixture 200 is provided. The process comprises:

Step (a) comprises optionally removing impurities from a carboxylic acid slurry 30 in an solid-liquid displacement zone 40 to form a slurry or cake carboxylic acid product 70 and a mother liquor stream 60;

The carboxylic acid slurry comprises 30 at least one carboxylic acid, catalyst, at least one solvent, and impurities. The impurities typically comprise at least one or more of the following compounds: 4-carboxybenzaldehyde (4-CBA), trimellitic acid (TMA), and 2,6-dicarboxyfluorenone (2,6-DCF). Suitable solvents include, but are not limited to, aliphatic mono-carboxylic acids, preferably containing 2 to 6 carbon atoms, or benzoic acid and mixtures thereof and mixtures of these compounds with water. Preferably the solvent is acetic acid mixed with water, in a ratio of about 5:1 to about 99:1, preferably between about 8:1 and about 49:1. Throughout the specification acetic acid will be referred to as the solvent. However, it should be appreciated that other suitable solvents, such as those disclosed previously, may also be utilized. The solvent typically comprises acetic acid, but can be any solvent that has been previously mentioned.

The carboxylic acid slurry 30 can be produced by oxidizing in a oxidation zone an aromatic feed stock. In one embodiment, the aromatic feedstock comprises paraxylene. The oxidation zone comprises at least one oxidation reactor, and the carboxylic acid slurry comprises at least one carboxylic acid. The oxidation reactor can be operated at temperatures between about 120° C. and about 250° C., preferably about 140° C. to about 170° C. Typically the aromatic feed stock comprises paraxylene and the carboxylic acid comprises terephthalic acid. In one embodiment of the invention the oxidation zone comprises a bubble column.

Therefore, for example, when terephthalic acid is utilized, the carboxylic acid slurry 30 would be referred to as terephthalic acid slurry and the carboxylic acid/diol mixture 200 would be referred to as a terephthalic acid/diol mixture.

Carboxylic acids include any carboxylic acid produced via controlled oxidation of an organic precursor compound. For example carboxylic acids include aromatic dicarboxylic acids preferably having 8 to 14 carbon atoms, aliphatic dicarboxylic acids preferably having 4 to 12 carbon atoms, or cycloaliphatic dicarboxylic acids preferably having 8 to 12 carbon atoms. Other examples of suitable carboxylic acids include, but are not limited to, terephthalic acid, benzoic, p-toluic, isophthalic acid, trimellitic acid, naphthalene dicarboxylic acid, cyclohexanedicarboxylic acid, cyclohexanediacetic acid, diphenyl-4,4'-dicarboxylic acid, diphenyl-3,4'-dicarboxylic acid, 2,2,-dimethyl-1,3-propandiol dicarboxylic acid, succinic acid, glutaric acid, adipic acid, azelaic acid, sebacic acid, and mixtures thereof.

Terephthalic acid slurry is conventionally synthesized via the liquid phase oxidation of paraxylene in the presence of suitable oxidation catalyst. Suitable catalysts include, but are not limited to, cobalt, manganese and bromine compounds, which are soluble in the selected solvent. In one embodiment of the invention the catalyst comprises cobalt, bromine and manganese. The cobalt and manganese combined can be in concentrations of about 100 ppm to about 2700 ppm by weight in the liquor. The bromine can be in concentrations of about 1000 ppm to about 2500 ppm by weight in the liquor.

The carboxylic acid slurry 30 is fed to a solid-liquid displacement zone 40 capable of removing a portion of the liquid contained in the carboxylic acid slurry 30 to produce a slurry or cake carboxylic acid product in conduit 70. The removal of a portion of the liquid to produce a slurry or cake carboxylic acid product in conduit 70 can be accomplished by any means known in the art. In an embodiment of the invention, as used herein, a portion means at least 5% by weight of the liquid is removed. Typically, the solid-liquid displacement zone 40 comprises a solid-liquid separator that is selected from the group consisting of a decanter centrifuge, rotary disk centrifuge, belt filter, rotary vacuum filter, and the like. The carboxylic acid slurry in conduit 30 is fed to the solid-liquid displacement zone 40 comprising at least one solid-liquid separator. The solid-liquid separator(s) can be operated at temperatures between about 50° C. to about 200° C., preferably 140° C. to about 170° C. The solid-liquid separator(s) can be operated at pressures between about 0 psig to about 200 psig. The solid-liquid separator in the solid-liquid displacement zone 40 may be operated in continuous or batch mode, although it will be appreciated that for commercial processes, the continuous mode is preferred.

The impurities are displaced from the solid-liquid displacement zone 40 into a mother liquor stream and withdrawn via line 60. In one embodiment of the invention, additional solvent is fed to the solid-liquid displacement zone 40 via line 50 to reslurry the carboxylic acid slurry 30 and form a slurry or cake carboxylic acid product 70. When a terephthalic acid slurry is utilized in the solid-liquid separation zone 40, a slurry or cake terephthalic acid product is produced. The slurry or cake terephthalic acid product typically comprises terephthalic acid and acetic acid. The mother liquor 60 is withdrawn from solid-liquid displacement zone 40 via line 60 and comprises a solvent, typically acetic acid, catalyst, and bromine compounds. The mother liquor in line 60 may either be sent to a process for separating impurities from oxidation solvent via lines not shown or recycled to the catalyst system via lines not shown. One technique for impurity removal from the mother liquor 60 commonly used in the chemical processing industry is to draw out or "purge" some portion of the recycle stream. Typically, the purge stream is simply disposed of or, if economically justified, subjected to various treatments to remove undesired impurities while recovering valuable components. Examples of impurity removal processes include U.S. Pat. No. 4,939,297 and U.S. Pat. No. 4,356,319, herein incorporated by reference.

Step (b) comprises removing in a solvent wash zone 80 residual impurities from a slurry or cake carboxylic acid product 70 to form a carboxylic acid cake with solvent 110 and a solvent mother liquor stream 100.

Conduit 70 contains a slurry or cake carboxylic acid product 70 comprising a carboxylic acid, residual impurities and a solvent. The residual impurities comprise residual catalyst (typically but not limited to cobalt, manganese, or bromine). Suitable solvents include, but are not limited to, aliphatic mono-carboxylic acids, preferably containing 2 to 6 carbon atoms, or benzoic acid and mixtures thereof and mixtures of these compounds with water. Preferably, the solvent is comprised of mainly acetic acid and/or some water. The ratio of acetic acid to water can range from 50:50 to 98:2 acetic acid to water by mass, more preferably in the range of 85:15 to 95:5, and most preferably in the range of 90:10 to 97:3. Suitable carboxylic acids include by are not limited to terephthalic acid, isophthalic acid, naphthalene dicarboxylic acid, trimellitic acid, and mixtures thereof.

The slurry or cake carboxylic acid product 70 is in the range of 10-90% by weight carboxylic acid. Preferably the slurry or cake carboxylic acid product 70 is in the range of 25-40% by weight carboxylic acid for a slurry and in the range of 70-90% by weight for the cake product. Most preferably, the slurry or cake carboxylic acid product 70 is in the range of 30-40% by weight carboxylic acid. The slurry or cake carboxylic acid product in conduit 70 is then introduced into a solvent wash zone 80, wherein a portion of solvent is recovered in the solvent mother liquor stream in conduit 100. The solvent mother liquor 102 comprises a portion of the solvent. In one embodiment of the invention, additional solvent can be added via conduit 90 counter current to the flow of the slurry or cake carboxylic acid product 70 in the solvent wash zone 80. The amount of stages of solvent counter current wash can be any amount of stages necessary to produce the carboxylic cake with solvent to the desired purity. Typically, the amount of stages in the solvent counter current wash can be about 1 to about 8, preferably about 2 to about 6, most preferably about 2 to about 4. For wash with more than one stage, counter current flow is preferable. Solvent counter current wash is preferable because typically it results in less solvent being used as compared to a process when solvent counter current wash is not utilized.

The solvent wash zone 80 comprises at least one solid-liquid separation device capable of efficiently separating solids and liquids. The solid-liquid separation device can typically be comprised of, but not limited to, the following types of devices: centrifuges, cyclones, rotary drum filters, belt filters, press filters, etc. The solvent wash zone 80 comprises at least one solid-liquid separation device(s) 110 which can operate within a temperature range of from approximately 40° C. to 155° C. Preferably the solid-liquid separation device(s) 110 can operate within a temperature range of from about 80° C. to about 150° C. Most preferably the solid-liquid separation device(s) 110 can operate within a temperature range of from about 90° C. to about 150° C. A carboxylic acid cake with solvent 110, is produced wherein the moisture composition of the carboxylic acid cake with solvent 110 can be in the range of 0.5-30% by weight moisture, preferably in the range of 1-20% moisture, most preferably in the range of 1-10% moisture. Optionally, the residual solvent can be removed by a gas displacement step to minimize solvent contamination with wash. When the carboxylic acid is terephthalic acid and the solvent is acetic acid a terephthalic acid cake with acetic acid is produced.

Step (c) comprises optionally removing a portion of a solvent in a water wash zone 120 from the carboxylic acid cake with solvent 110 to form a water-wet carboxylic acid cake 100 and a solvent/water byproduct liquor stream 140.

The carboxylic acid cake with solvent 110, is then subjected to a wash or "rinsing" with water or water with residual amounts of solvent in the water wash zone 120, wherein a portion of the solvent is replaced with water to form a water-wet carboxylic acid cake 150. The water-wet carboxylic acid cake 150, is preferably in the range of about 0.5% to about 30% moisture, more preferably in the range of about 1 to about 20% moisture, and most preferably in the range of about 1% to about 10% moisture. The residual moisture of the water-wet carboxylic acid cake 150, should contain less than about 2% solvent on a mass basis. Additionally, the water-wet carboxylic acid cake 150 should contain less than 1% of any metals, preferably less than 100 ppm by weight, most preferably less than 10 ppm by weight, typically used as catalysts in p-xylene oxidation, in the slurry or cake carboxylic acid product in conduit 70, should remain in the water-wet carboxylic acid cake 150. Examples of metals include but are not limited to cobalt, and manganese.

Wash water is introduced into the water wash zone 120 via conduit 130. The wash water should be, on a continuous basis, comprise a mass feed rate in ratio with the solids in the carboxylic cake with solvent 110 in the range of about 0.1:1 to about 1.5:1, preferably in the range of about 0.1:1 to about 0.6:1, most preferably in the range of about 0.2:1 to about 0.4:1. There are no limitations on the temperature or pressure of the wash water including the use of vaporized water, steam, or a combination of water and steam, as wash. In one embodiment of the invention, wash water is introduced counter current to the carboxylic acid cake with solvent.

Additional wash water can be added via conduit 130 counter current to the flow of the carboxylic acid cake with solvent 110 in the water wash zone 120. The amount of stages of water counter current wash can be any amount of stages necessary to produce the water wet carboxylic acid cake to the desired purity. Typically, the amount of stages in the water counter current wash can be about 1 to about 8, preferably about 2 to about 6, most preferably about 2 to about 4. For wash with more than one stage, counter current flow is preferable. Water counter current wash is preferable because typically it results in less water being used as compared to a process when water counter current wash is not utilized.

The water wash zone comprises a solid-liquid separation device 120 can typically be comprised of, but not limited to, the following types of devices: centrifuges, cyclones, rotary drum filters, belt filters, press filters, etc. The solid-liquid separation device can be operated within a temperature range of from about 40° C. to about 155° C. Preferably, the second solid-liquid separation device can operate within a temperature range of from about 80° C. to about 150° C. Most preferably, the second solid-liquid separation device can operate within a temperature range of from about 90° C. to about 150° C.

Optionally, the solvent/water byproduct liquor from the water wash zone 120, is segregated from the solvent mother liquor stream produce by the solvent wash zone 80.

Step (d) comprises routing the water-wet carboxylic acid cake 150 to a vapor seal zone 160.

The water-wet carboxylic acid cake 150 is passed through a vapor seal zone 160 comprising a vapor seal device, and exits the vapor seal device via conduit 170. The vapor seal device allows the water-wet carboxylic acid cake 150 to exit the counter current wash zone 120 but prevents diol from the carboxylic acid/diol mixing zone 180 from entering the counter current wash zone or any process zone proceeding the vapor seal zone 160. The vapor seal device can be any device known in the art. Examples include, but are not limited to rotary air lock valve, and solid conveying extruders.

Step (e) comprises adding at least one diol 190 to the water-wet carboxylic acid cake 170 in a carboxylic acid/diol mixing zone 180 to remove a portion from the water-wet carboxylic acid cake 170 of the water to form the carboxylic acid/diol mixture 200.

Finally, the water-wet carboxylic acid cake 170, which is now substantially free of solvent is combined with a diol 190 in a carboxylic acid mixing zone 180, to form a carboxylic acid/diol mixture 200 suitable for PET production and other polyesters or co-polyesters. There are no special limitations on the carboxylic acid/diol mixing zone 180 with the exception that it comprises a device that must provide intimate contact between the water-wet carboxylic acid cake 170, and the diol 190 to produce a the carboxylic acid/diol mixture 200. Examples of such devices include, but are not limited to the following: an agitated vessel, static mixer, screw conveyor, PET esterification reactor(s), etc. A solid eductor could be used to introduce the water-wet carboxylic acid cake into the device. Nor is there any specific limitation on the temperature range at which the device can operate. However, it is preferable that the temperature of device does not exceed approximately 280° C., temperatures normally found within PET esterification reactors. As used herein, in one embodiment of the invention, a portion of the water can mean any part up to and including the whole. In another embodiment of the invention a portion can mean at least 5% by weight. In another embodiment of the invention a portion can mean at least 10% by weight. In another embodiment of the invention a portion can mean at least 25% by weight. In another embodiment of the invention a portion can mean at least 50% by weight. In another embodiment of the invention, a portion can mean at least 75% by weight. In another embodiment of the invention a portion can mean at least 85% by weight. In another embodiment of the invention a portion can mean at least 90% by weight. T At least one diol in conduit 190 can be introduced in such a manner as to optionally displace the water as the dominant slurrying liquid. This can be accomplished by introducing a diol via conduit 190 as a saturated liquid at a temperature which is sufficient to vaporize the water. In one embodiment of the invention, the diol in conduit 190 is introduced as a saturated or superheated vapor. The diol in conduit 190 is at least one selected from the group consisting of ethylene glycol, diethylene glycol, n-butylene glycol, i-butylene glycol, n-propylene glycol, 1,4 butanediol, cyclohexanedimethanol, and mixtures thereof. Preferably, the diol in conduit 190 is ethylene glycol. Note that within the system shown in FIG. 1, a substantially dry carboxylic acid solid is not formed. In one embodiment of the invention substantially dry generally means less than 5% by weight moisture. In another embodiment of the invention, another range can be less than 10% by weight moisture. In another embodiment of the invention, still another range can be less than 15% by weight moisture. In another embodiment of the invention, yet another range for substantially dry can mean less than 20% by weight moisture. In another embodiment of the invention, another range for substantially dry can mean less than 25% by weight moisture. In yet another embodiment of the substantially dry would be the moisture content obtained through the use of mostly mechanical means for drying and wherein the majority of the drying is not accomplished through evaporation. Majority as used herein means greater than 50%. The primary advantage in not forming a carboxylic acid dry solid is the elimination of solids handling equipment. Examples of solids handing equipment include but are not limited to a dryer, convey systems, and silos.

In other embodiments of this invention step (a), step (b) and step (c) can be combined into one zone known as the liquor exchange zone 250 as shown in FIG. 2. The liquor exchange zone 250 comprises at least one solid-liquid separation device capable of performing the combined function of the solid-liquid separation zone 40, the solvent wash zone 80 and the water wash zone 120 as previously described. Step (b) and step (c) can also be combined into one zone known as the solvent-water liquor exchange zone 260 as shown in FIG. 3. Finally step (a) and step (b) can be combined into one zone known as the solvent liquor exchange zone 270 as show in FIG. 4. In each of the above embodiments comprises at least one solid-liquid separation device capable of performing the functions of the combined zones as previously described. Examples of devices that can be used in the liquor exchange zone 250, or the solvent-water liquor exchange zone 260, or the solvent liquor exchange zone 270 included but are not limited to, the following type of devices centrifuges, cyclones, filters, and such or combination thereof.

We claim:

1. A process for producing a carboxylic acid/diol mixture, said process comprising:
   (a) removing in a liquor exchange zone impurities from a carboxylic acid slurry to form a water-wet carboxylic acid cake, a mother liquor stream, a solvent mother liquor stream, and a solvent/water byproduct liquor stream; wherein said liquor exchange zone comprises at least one solid liquid separation device operated at a temperature of 50° C. to 200° C.;
   (b) routing said water-wet carboxylic acid cake to a vapor seal zone; and
   (c) adding at least one diol to said water-wet carboxylic acid cake in a carboxylic acid/diol mixing zone to form said carboxylic acid/diol mixture; wherein said diol displaces water from said water-wet carboxylic acid cake; and wherein said carboxylic acid/diol mixture is produced without the isolation of a substantially dry carboxylic acid solid; and where said vapor seal zone prevents said diol from entering any zone proceeding said vapor seal zone.

2. A process according to claim 1 wherein said carboxylic acid is selected from a group consisting of terephthalic acid, isophthalic acid, naphthalene dicarboxylic acid, trimellitic acid, and mixtures thereof.

3. A process according to claim 1 or 2 wherein said diol is selected from the group consisting of ethylene glycol, diethylene glycol, n-butylene glycol, i-butylene glycol, n-propylene glycol, 1,4 butanediol, cyclohexanedimethanol, and mixtures thereof.

4. A process according to claim 1 wherein said carboxylic acid/diol mixing zone comprises at least one device selected from the group consisting of an agitated vessel, a static mixer, and a screw conveyor.

5. A process according to claim 1 wherein said carboxylic acid is terephthalic acid and said diol is ethylene glycol.

6. A process for producing a carboxylic acid/diol mixture, said process comprising:
   (a) removing in a solvent liquor exchange zone impurities from a carboxylic acid slurry to form a carboxylic acid cake with solvent, a mother liquor stream, and a solvent mother liquor stream; wherein said liquor exchange zone comprises at least one solid liquid separation device operated at a temperature of 50° C. to 200° C.;
   (b) adding water in a water wash zone to said carboxylic cake with solvent to produce a water-wet carboxylic acid cake and a solvent/water by product liquor stream;
   (c) routing said water-wet carboxylic acid cake to a vapor seal zone; and
   (d) adding at least one diol to said water-wet carboxylic acid cake in a carboxylic acid/diol mixing zone to form said carboxylic acid/diol mixture; wherein said diol displaces water from said water-wet carboxylic acid cake; and wherein said carboxylic acid/diol mixture is produced without the isolation of a substantially dry carboxylic acid solid; and where said vapor seal zone prevents said diol from entering any zone proceeding said vapor seal zone.

7. A process according to claim 6 wherein said carboxylic acid is selected from a group consisting of terephthalic acid, isophthalic acid, naphthalene dicarboxylic acid, trimellitic acid and mixtures thereof.

8. A process according to claim 6 or 7 wherein said diol is selected from the group consisting of ethylene glycol, diethylene glycol, n-butylene glycol, i-butylene glycol, n-propylene glycol, 1,4 butanediol, cyclohexanedimethanol, and mixtures thereof.

9. A process according to claim 6 wherein said carboxylic acid/diol mixing zone comprises at least one device selected from the group consisting of an agitated vessel, a static mixer, and a screw conveyor.

10. A process according to claim 6 wherein said carboxylic acid is terephthalic acid and said diol is ethylene glycol.

11. A process for producing a carboxylic acid/diol mixture, said process comprising:
    (a) removing in a solid-liquid separation zone impurities from a carboxylic acid slurry to form a slurry or cake carboxylic acid product and a mother liquor stream; wherein said liquor exchange zone comprises at least one solid liquid separation device operated at a temperature of 50° C. to 200° C.;
    (b) removing in a solvent-water liquor exchange zone residual impurities from said slurry or cake carboxylic acid product to form a water-wet carboxylic acid cake, a solvent mother liquor stream, and a solvent/water byproduct liquor stream;
    (c) routing said water-wet carboxylic acid cake to a vapor seal zone; and
    (d) adding at least one diol to said water-wet carboxylic acid cake in a carboxylic acid/diol mixing zone to form said carboxylic acid/diol mixture; wherein said diol displaces water from said water-wet carboxylic acid cake; and wherein said carboxylic acid/diol mixture is produced without the isolation of a substantially dry carboxylic acid solid; and where said vapor seal zone prevents said diol from entering any zone proceeding said vapor seal zone.

12. A process according to claim 11 wherein said carboxylic acid is selected from a group consisting of terephthalic acid, isophthalic acid, naphthalene dicarboxylic acid, trimellitic acid and mixtures thereof.

13. A process according to claim 11 or 12 wherein said diol is selected from the group consisting of ethylene glycol, diethylene glycol, n-butylene glycol, i-butylene glycol, n-propylene glycol, 1,4 butanediol, cyclohexanedimethanol, and mixtures thereof.

14. A process according to claim 11 wherein said carboxylic acid/diol mixing zone comprises at least one device selected from the group consisting of an agitated vessel, a static mixer, and a screw conveyor.

15. A process according to claim 11 wherein said carboxylic acid is terephthalic acid and said diol is ethylene glycol.

16. A process for producing a carboxylic acid/diol mixture, said process comprising the following steps:
    (a) removing a solvent from a slurry or cake carboxylic acid product in a solvent-water liquor exchange zone; wherein a portion of the solvent in said slurry or cake carboxylic acid product is replaced with water to form a water-wet carboxylic acid cake;
    (b) routing said water-wet carboxylic acid cake to a vapor seal zone; and
    (c) adding at least one diol to said water-wet carboxylic acid cake in a carboxylic acid/diol mixing zone to form said carboxylic acid/diol mixture; wherein said diol displaces water from said water-wet carboxylic acid cake;

and wherein said carboxylic acid/diol mixture is produced without the isolation of a substantially dry carboxylic acid solid; and where said vapor seal zone prevents said diol from entering any zone proceeding said vapor seal zone; wherein said carboxylic acid/diol mixing zone comprises at least one device selected from the group consisting of an agitated vessel, a static mixer, and a screw conveyor.

17. A process according to claim 16 wherein said carboxylic acid is selected from a group consisting of terephthalic acid, isophthalic acid, naphthalene dicarboxylic acid, trimellitic and mixtures thereof.

18. A process according to claim 16 or 17 wherein said diol is selected from the group consisting of ethylene glycol, diethylene glycol, n-butylene glycol, i-butylene glycol, n-propylene glycol, 1,4 butanediol, cyclohexanedimethanol, and mixtures thereof.

19. A process for producing a terephthalic acid/diol mixture, said process comprising:
    (a) removing in a solvent wash zone residual impurities from a slurry or cake terephthalic acid product to form a terephthalic acid cake with acetic acid; wherein said liquor exchange zone comprises at least one solid liquid separation device operated at a temperature of 50° C. to 200° C.;
    (b) removing a portion of a solvent in a water wash zone from said terephthalic acid cake with acetic acid to form a water-wet terephthalic acid cake; and
    (c) routing said water-wet terephthalic acid cake to a vapor seal zone; and
    (d) adding at least one diol to said water-wet terephthalic acid cake in a carboxylic acid/diol mixing zone to form said terephthalic acid/diol mixture; wherein said diol displaces water from said water-wet carboxylic acid cake; and wherein said carboxylic acid/diol mixture is produced without the isolation of a substantially dry carboxylic acid solid; and where said vapor seal zone prevents said diol from entering any zone proceeding said vapor seal zone.

20. A process according to claim 19 wherein said solvent wash zone comprises a solid-liquid separation device that is operated at a temperature between about 40° C. to about 155° C.

21. A process according to claim 20 wherein said water wash zone comprises a solid-liquid separation device that is operated at a temperature between about 40° C. to about 155° C.

22. A process according to claim 19 or 20 wherein said adding occurs at a temperature between about 40° C. to about 290° C.

23. A process according to claim 19 wherein said diol is selected from the group consisting of ethylene glycol, diethylene glycol, n-butylene glycol, i-butylene glycol, n-propylene glycol, 1,4 butanediol, cyclohexanedimethanol, and mixtures thereof.

24. A process according to claim 19 wherein said diol is ethylene glycol.

25. A process according to claim 19 wherein said carboxylic acid/diol mixing zone comprises a device selected from the group consisting of an agitated vessel, a static mixer, and a screw conveyor.

26. A process for producing a terephthalic acid/diol mixture, said process comprising:
    (a) removing a solvent from a slurry or cake terephthalic acid product in a solvent-water liquor exchange zone; wherein a portion of the solvent in said slurry or cake terephthalic acid product is replaced with water to form a water-wet terephthalic acid cake; wherein said liquor exchange zone comprises at least one solid liquid separation device operated at a temperature of 50° C. to 200° C.;
    (b) routing said water-wet terephthalic acid cake to a vapor seal zone; and
    (c) adding at least one diol to said water-wet terephthalic acid cake in a carboxylic acid/diol mixing zone to form said terephthalic acid/diol mixture; wherein said diol displaces water from said water-wet terephthalic acid cake; and wherein said terephthalic acid/diol mixture is produced without the isolation of a substantially dry terephthalic acid solid; and where said vapor seal zone prevents said diol from entering any zone proceeding said vapor seal zone.

27. A process according to claim 26 wherein said solvent liquor exchange zone comprises a solid-liquid separation device that is operated at a temperature between about 40° C. to about 155° C.

28. A process according to claim 26 wherein said adding occurs at a temperature between about 40° C. and 290° C.

29. A process according to claim 26 wherein said diol is selected from the group consisting of ethylene glycol, diethylene glycol, n-butylene glycol, i-butylene glycol, n-propylene glycol, 1,4 butanediol, cyclohexanedimethanol, and mixtures thereof.

30. A process according to claim 26 wherein said diol is ethylene glycol.

* * * * *